US008946456B2

(12) United States Patent
Ciambecchini et al.

(10) Patent No.: US 8,946,456 B2
(45) Date of Patent: Feb. 3, 2015

(54) PROCESS FOR THE PREPARATION OF 2-HYDROXY-4-PHENYL-3,4-DIHYDRO-2H-CHROMEN-6-YL-METHANOL AND (R)-FESO-DEACYL

(75) Inventors: Umberto Ciambecchini, Patrica (IT); Stefano Turchetta, Patrica (IT); Lorenzo De Ferra, Patrica (IT); Maurizio Zenoni, Patrica (IT)

(73) Assignee: Chemi S.p.A., Cinisello Balsamo (MI) (IT)

( * ) Notice: Subject to any disclaimer, the term of this patent is extended or adjusted under 35 U.S.C. 154(b) by 0 days.

(21) Appl. No.: 13/702,403

(22) PCT Filed: Apr. 29, 2011

(86) PCT No.: PCT/IB2011/051896
§ 371 (c)(1),
(2), (4) Date: Dec. 6, 2012

(87) PCT Pub. No.: WO2011/154854
PCT Pub. Date: Dec. 15, 2011

(65) Prior Publication Data
US 2013/0079532 A1    Mar. 28, 2013

(30) Foreign Application Priority Data
Jun. 10, 2010 (IT) .............................. MI2010A1047

(51) Int. Cl.
C07D 311/20 (2006.01)
C07C 213/10 (2006.01)
C07C 213/00 (2006.01)
C07C 213/02 (2006.01)
C07C 215/54 (2006.01)

(52) U.S. Cl.
CPC .............. *C07D 31/20* (2013.01); *C07C 213/00* (2013.01); *C07C 213/02* (2013.01); *C07C 213/10* (2013.01); *C07C 215/54* (2013.01)
USPC ............................ 549/399; 560/142; 564/316

(58) Field of Classification Search
USPC ........................................................ 549/399
See application file for complete search history.

(56) References Cited

U.S. PATENT DOCUMENTS 6,858,650 B1    2/2005  Meese
2006/0160838 A1 *  7/2006  Schlachter et al. ........... 514/291

FOREIGN PATENT DOCUMENTS

| EP | 0 957 073 A1 | 11/1999 |
| WO | WO 2004012735 A2 * | 2/2004 |
| WO | 2007/138440 A1 | 12/2007 |
| WO | WO 2007138440 A1 * | 12/2007 |
| WO | 2010/018484 A1 | 2/2010 |

OTHER PUBLICATIONS

Turner, A.B., Quinone Methides, Q. Rev. Chem. Soc. 1964, 18, 347-360.*
Lorentz, L.F., Accelerated Cure of Phenol-Formaldehyde by the Addition of Cure Accelerators: Studies with Model Compounds, Technical Forum Presentations, Wood Adhesives 2000, 391-395.*
Xiao, M., Facile Synthesis of Anticancer Drug NCX 4040 in Mild Conditions, Lett. Org, Chem., 2008, 5, 510-513.*
Periasamy, M., Methods of enhancement of reactivity and selectivity of sodium borohydride for applications in organic synthesis, J. Org. Metall. Chem., 2000, 606, 137-151.*
Crouch, D. R., "Selective monodeprotection of bis-silyl ethers." Tetrahedron 60.28 (2004): 5833-5871.*
Kawazoe, et al., "Selective Desilylation of Phenolic and Alcoholic Trimethylsilyl Ethers," Tetrahedron Letters, vol. 28, No. 37, pp. 4307-4310, 1987 (XP002615925).

* cited by examiner

*Primary Examiner* — Noble Jarrell
*Assistant Examiner* — John Mauro
(74) *Attorney, Agent, or Firm* — Silvia Salvadori, P.C.

(57) ABSTRACT

The present invention regards an improved and industrially advantageous process for the preparation of the 2-hydroxy-4-phenyl-3,4-dihydro-2H-chromen-6-yl-methanol intermediates, also called "feso chromenyl" and (R)-2-[3-(diisopropylamino)-1-phenylpropyl]-4-(hydroxymethyl)phenol, also called "(R)-feso deacyl", which are in turn used in the synthesis of fesoterodine and in particular of fesoterodine fumarate. This process utilises reagents which are non-toxic and manageable at industrial level and enables obtaining a new stable and non-hygroscopic crystalline form of the key intermediate "(R)-feso deacyl", called form B.

12 Claims, 8 Drawing Sheets

PXRD of (R)-2-[3-(diisopropylamino)-1-phenylpropyl]-4-(hydroxymethyl)phenol in crystalline form A DSC of (R)-2-[3-(diisopropylamino)-1-phenylpropyl]-4-(hydroxymethyl)phenol in crystalline form A TGA of (R)-2-[3-(diisopropylamino)-1-phenylpropyl]-4-(hydroxymethyl)phenol in crystalline form A FT-IR (ATR) of (R)-2-[3-(diisopropylamino)-1-phenylpropyl]-4-(hydroxymethyl)phenol in crystalline form A PXRD of (R)-2-[3-(diisopropylamino)-1-phenylpropyl]-4-(hydroxymethyl)phenol in crystalline form B DSC of (R)-2-[3-(diisopropylamino)-1-phenylpropyl]-4-(hydroxymethyl)phenol in crystalline form B TGA of (R)-2-[3-(diisopropylamino)-1-phenylpropyl]-4-(hydroxymethyl)phenol in crystalline form B FT-IR (ATR) of (R)-2-[3-(diisopropylamino)-1-phenylpropyl]-4-(hydroxymethyl)phenol in crystalline form B

PROCESS FOR THE PREPARATION OF 2-HYDROXY-4-PHENYL-3,4-DIHYDRO-2H-CHROMEN-6-YL-METHANOL AND (R)-FESO-DEACYL

This application is a U.S. National Stage of PCT/IB2011/051896 filed Apr. 29, 2011, which claims priority to and the benefit of Italian Application No. MI2010A001047 filed Jun. 10, 2010, the contents of which applications are incorporated herein by reference in their entirety.

The present invention regards an improved and industrially advantageous process for the preparation of the 2-hydroxy-4-phenyl-3,4-dihydro-2H-chromen-6-yl-methanol intermediates, also called "feso chromenyl" and (R)-2-[3-(diisopropylamino)-1-phenylpropyl]-4-(hydroxymethyl)phenol, also called "(R)-feso deacyl", which are in turn used in the synthesis of the fesoterodine and in particular of the fesoterodine fumarate. This process utilises reagents which are non-toxic and manageable at industrial level and enables obtaining a new stable and non-hygroscopic crystalline form of the key intermediate "(R)-feso deacyl", called form B.

STATE OF THE ART

Fesoterodine fumarate is the international non-proprietary name (INN) of the 2-[(R)-3-diisopropylammonio-1-phenylpropyl)-4-(hydroxymethyl)phenylisobutyrate hydrogen fumarate active ingredient, whose structural formula is indicated below.

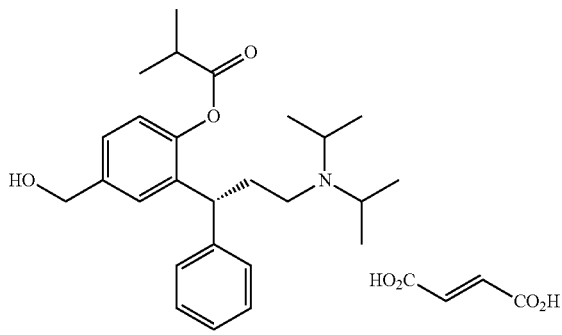

Fesoterodine fumarate was approved in Europe and in the USA for the treatment of overactive bladder syndrome under the commercial name of TOVIAZ®.

Fesoterodine fumarate was described for the first time in U.S. Pat. No. 6,858,650, herein incorporated for reference, which discloses the preparation of the active ingredient through the salification of fesoterodine with fumaric acid, according to the scheme indicated below.

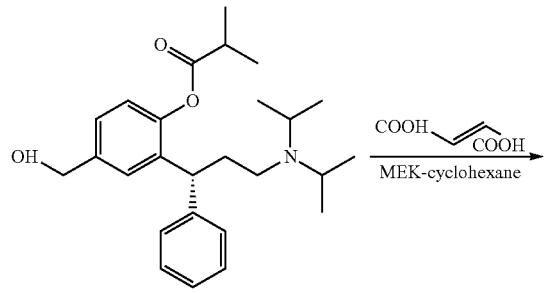

In turn, the preparation of fesoterodine (also called base fesoterodine) is described in U.S. Pat. No. 6,713,464, incorporated herein for reference, where it is prepared starting from the deacylated precursor (R)-feso deacyl, according to the scheme indicated below.

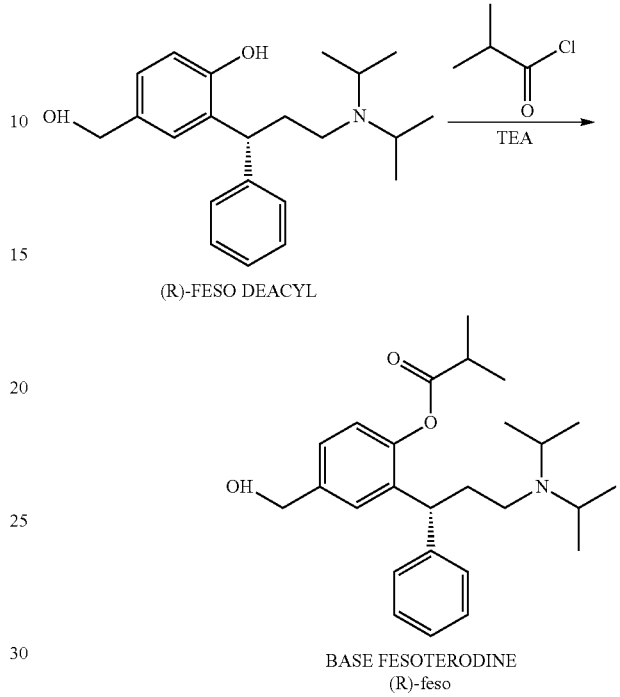

deacyl constitutes a key intermediate for the preparation of fesoterodine fumarate.

The preparation of the (R)-feso deacyl is described for the first time in U.S. Pat. No. 5,559,269. In this patent it is prepared from para-bromophenol; the relative synthetic process consists of numerous steps. In addition, it utilises reagents that are difficult to use at industrial level such as lithium aluminium hydride and Grignard reagents.

The preparation of (R)-feso deacyl can be conducted according to the description disclosed in U.S. Pat. No. 6,809,214. But also in this case, the synthesis reveals disadvantages due to the utilisations that are difficult to implement at industrial level such as DIBAL, lithium aluminium hydride and expensive resolvent agents such as cinchonidine.

Taking cue from the syntheses known in the art, it is observable that the brief synthesis for the preparation of (R)-feso deacyl could also be provided starting from 2-hydroxy-4-phenyl-3,4-dihydro-2H-chromen-6-yl-methanol, also called "feso chromenyl", described in the scheme indicated below.

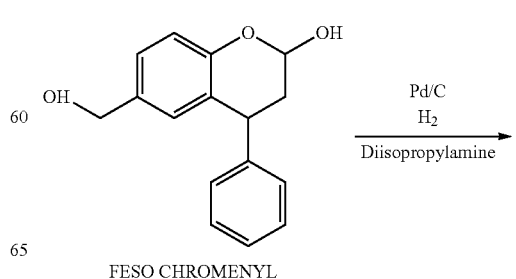

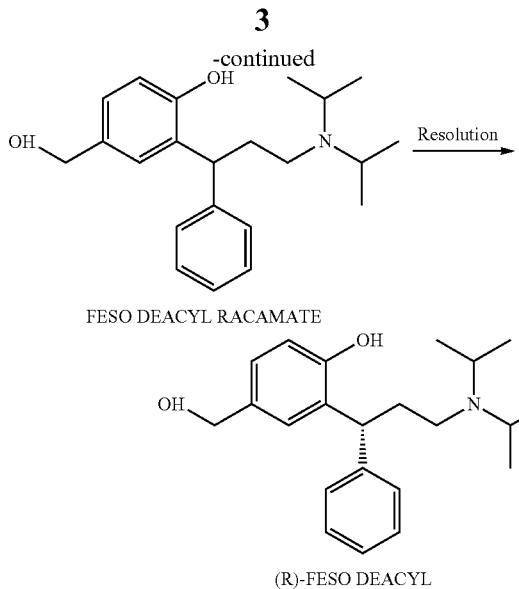

FESO DEACYL RACAMATE (R)-FESO DEACYL

In literature various methods used for obtaining intermediates referable to feso chromenyl worth mentioning include Jurd's article which discloses the reaction between phenols, cinnamaldehyde and morpholine to prepare 2-morpholinyl-4-phenylbenzopyranes (*Journal of Heterocyclic Chemistry*, vol 28 (4), page 983-986 (1991)).

Following such reference literature, WO2007138440 describes the preparation of fesoterodine by using (2-hydroxy-4-phenyl-3,4-dihydro-2H-chromen-6-yl)methanol.

Such synthesis, with respect to what is known in the prior art, is apparently advantageous in that it requires few steps and the use of common reagents. However, the yield indicated in WO2007138440 for (R)-feso deacyl amounts to 12%. Such yield is unsatisfactory in terms of industrial application, and it is essentially due to the low yield of the passage regarding the preparation of the feso chromenyl derivative, which is equivalent to 53.4%.

Thus, there still arises the need for providing an efficient method, capable of utilising reagents that can be used at industrial level for the synthesis of (R)-Feso deacyl.

DESCRIPTION

Figure 1:
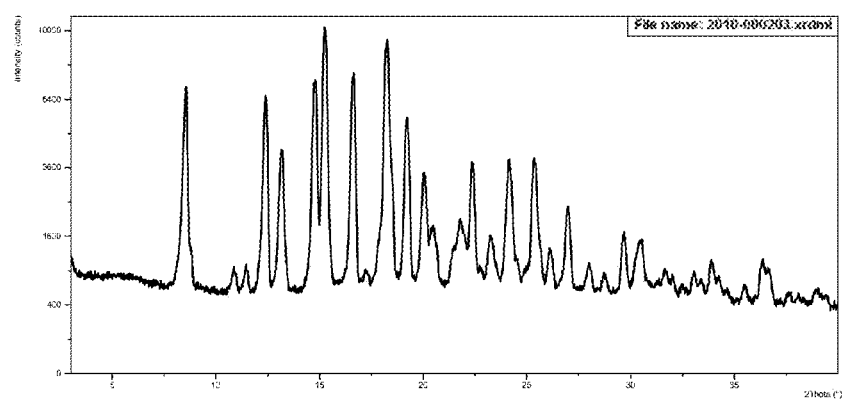
FIG. 1: PXRD of the crystalline form A of the (R)-feso-deacyl

Now, a new process for the preparation of feso-chromenyl, in a few steps and using reagents manageable at industrial level has been surprisingly discovered.

With the aim of improving the synthesis described in WO2007138440, in particular regarding the step of synthesis from 4-hydroxymethylphenol to feso chromenyl it was surprisingly discovered that protecting the methylene group of the 4-hydroxymethylphenol with a silylated group and subjecting such product to the reaction with cinnamaldehyde and morpholine allows obtaining (2-hydroxy-4-phenyl-3,4-dihydro-2H-chromen-6-yl)methanol i.e. feso chromenyl, with yields exceeding 60%.

A schematic description of this new method of synthesis is indicated in the scheme below.

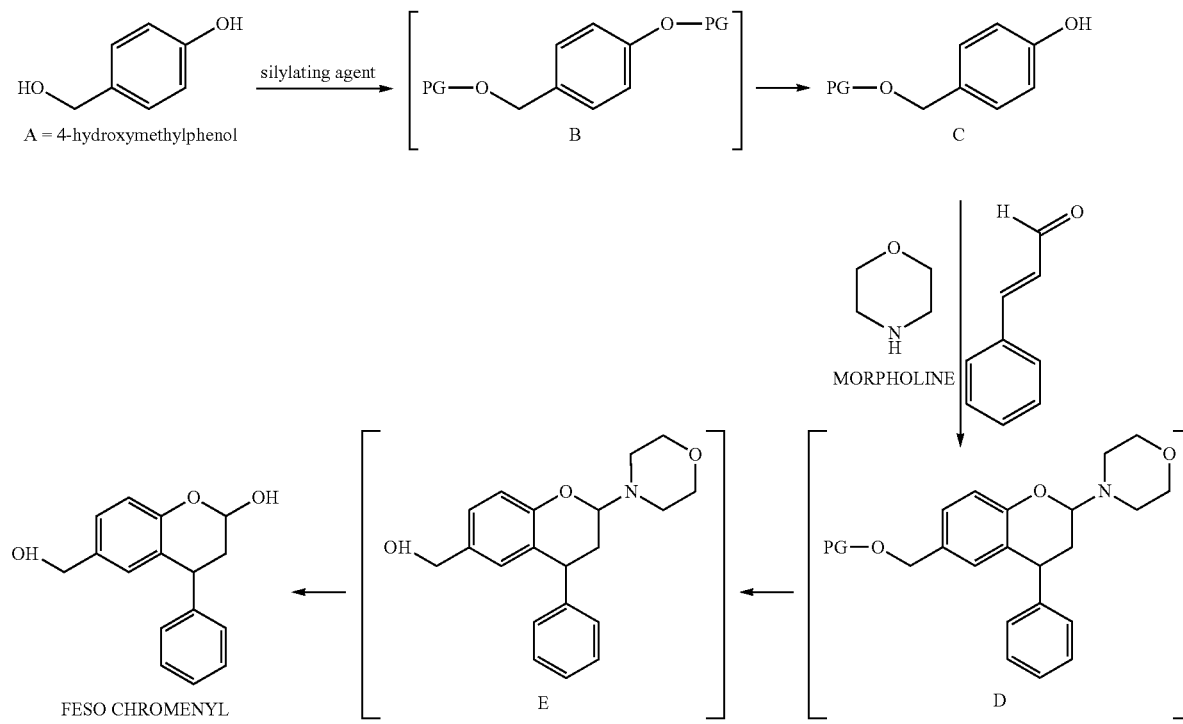

The silylated protective groups of the hydroxyls, i.e. the silyl ethers, just like corresponding deprotection methods, are well known in literature and are described, for example, in Green et al. *Protective groups in organic synthesis*, 3$^{rd}$ Edition, pages 113-148, Wiley Interscience, 1999, herein incorporated for reference. Regarding the present invention, the term "silylating agent" is thus used to indicate any reagent capable of forming a silyl ether with the hydroxyl functions of the p-hydroxymethyl phenol. Examples of silylating agents are:

$R_1R_2R_3SiX$ wherein $R_1$, $R_2$ and $R_3$ are groups equal or different from each other and represent linear or branched $C_1$-$C_6$ alkyl or variously substituted aryl residues and X is a halogen or a sulfonate group such as methanesulfonate or trifluoromethanesulfonate; preferred examples are chlorotrimethylsilane, chlorotriethylsilane, t-butyl-dimethyl-silyl chloride, t-butyl-diphenyl-silyl chloride, trimethylsilyl triflate.

$CY_3CO(Me_3Si)=NH(Me_3Si)$, represents reagents wherein Y can be hydrogen or halogens, such as bis trimethylsilylacetamide and bis-trimethylsilyl-trifluoroacetamide.

$(Me_3SiNH)_2C=O$, i.e. the bis-trimethylsilylurea.

The silylating agents particularly preferred regarding the present invention are trimethylsilyl chloride and t-butyl-dimethyl silyl chloride.

The term PG is used to indicate a silylated protective group obtained after the reaction of the p-hydroxymethyl phenol with a silylating agent and, in particular, with one of the silylating agents described above. For example, using a compound of the $R_1R_2R_3SiX$ type as the silylating agent, the PG group derived therefrom is —$SiR_1R_2R_3$.

The expression "one pot" is used to indicate a series of consecutive reactions in which the different intermediates are not isolated.

The 4-hydroxymethylphenol of formula (A), available in the market,

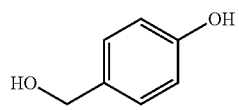
(A)

is reacted with a silylating agent. In a preferred embodiment of the present invention, the silylating agent is reacted in presence of a base. Said base is preferably an organic base, even more preferably an amine, such as triethylamine, dimethylaminopyridine, imidazole and/or diisopropylethylamine. The sylilating agent: 4-hydroxymethylphenol molar ratio is comprised between 2 and 3 equivalents, preferably between 2 and 2.5 equivalent.

The solvent is preferably an apolar solvent, even more preferably dichloromethane; the reaction is preferably conducted at a temperature comprised between 0° C. and ambient temperature, even more preferably between 0° C. and 10° C.

This allows obtaining the bis-silylated intermediate of formula (B),

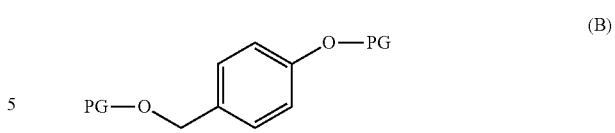
(B)

which preferably is not isolated.

The bis-silylated intermediate of formula (B) is thus selectively deprotected on the phenolic hydroxyl. Such deprotection occurs, preferably, by reacting the bis-silylated intermediate of formula (B) with a salt of alkaline metals, even more preferably lithium acetate or cesium carbonate.

The solvent is preferably an aprotic polar solvent, optionally mixed with water, even more preferably dimethylformamide; the reaction is preferably conducted at ambient temperature, even more preferably at a temperature comprised between 20 and 30° C., even more preferably at about 25° C.

Hence enabling obtaining the monosilylated derivative of formula (C)

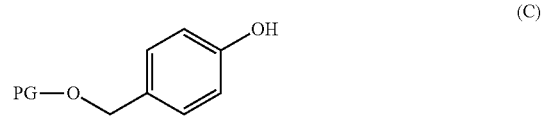
(C)

The monosilylated derivative of formula (C) thus obtained is subjected to reaction with trans-cinnamaldehyde and a secondary cyclic amine of formula (F)

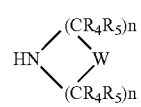
(F)

wherein
$R_4$ and $R_5$ equal or different from each other are hydrogen, $C_1$-$C_6$ alkyl or aryl and n varies between 1 and 4;
W is $(CH_2)_m$ with m varying between 0 and 1, $NR_6$ (with $R_6=C_1$-$C_6$ alkyl or aryl), O or S.

to obtain the addition-condensation compound of formula (D),

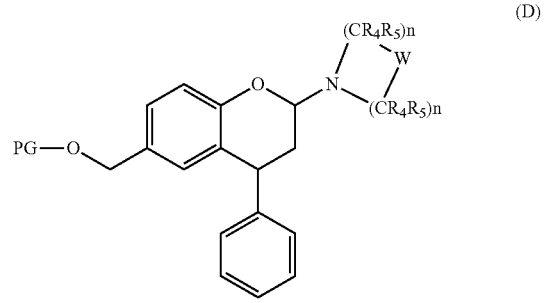
(D)

According to a preferred embodiment, $R_4$ and $R_5$ are both H, n is 2 and W is O.

Examples of preferred cyclic secondary amines are morpholine, N-methyl-piperazine, N-benzyl-piperazine, pyrrolidine, piperazine and the like, preferably it is morpholine. The secondary amine:monosilylated derivative of formula (C)

molar ratio is comprised between 2 and 3 equivalents, preferably between 2.5 and 3 equivalents.

The solvent is preferably an apolar organic solvent, even more preferably toluene; the reaction is preferably conducted at a temperature comprised between 70° C. and reflux temperature of the solvent, even more preferably between 90° C. and 110° C.

The compound of formula (D) is then converted, by removing the silylated protective group in the compound of formula (E)

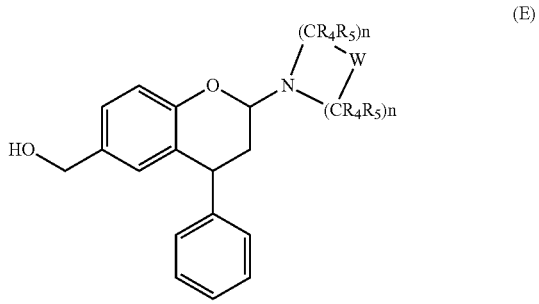

which, is in turn transformed into the desired feso chromenyl compound through hydrolysis, preferably in an acid environment.

The removal of the silylated protective group may occur simultaneously with the hydrolysis of the amine portion, in the case where the silylated protective group is labile in diluted acid aqueous conditions (for example when the silylated protective group is $Me_3Si$) in which the hydrolysis of the compound (E) is carried out.

Alternatively, the removal of the silylated protective group occurs by reacting with fluoride ion, preferably with tetrabutylammonium fluoride. The solvent is preferably a mixture of aliphatic or aromatic hydrocarbon and an ether, even more preferably a toluene-THF mixture; the reaction is preferably conducted at a temperature comprised between ambient temperature and reflux temperature, even more preferably between 30° C. and 60° C.

The hydrolysis of the compound of formula (E) is conducted by mixing the reaction mixture with an aqueous solution having a pH below 1. According to an aspect of the invention, 5 to 100 volumes of aqueous solution per volume of reaction mixture are used, preferably 10 volumes. According to a further aspect of the invention, such pH is obtained using strong acids, such as hydrochloric acid, hydrobromic acid, sulphuric acid and the like. According to a particularly preferred aspect of the invention, said aqueous solution is a hydrochloric acid aqueous solution at 5%.

In a preferred embodiment of the present invention, the intermediates of formula (B), (D) and/or (E) are not isolated.

A further object of the present invention is a new process for the preparation of the (R)-feso-deacyl, starting from feso chromenyl.

Any method known to a man skilled in the art can be used to convert feso chromenyl into (R)-feso-deacyl, such as for example the methods described in WO2007138440, herein incorporated for reference.

However, it was observed that in the synthetic passage from feso chromenyl intermediate to the feso deacyl raceme which utilises diisopropylamine in presence of hydrogen and catalyst, considerable amounts of the reduction product of the $CH_2OH$ are also generated.

In the study of optimisation of this synthetic passage, is it was unexpectedly discovered that the transformation of feso chromenyl into feso deacyl raceme can be conveniently conducted through reductive amination of feso chromenyl with diisopropylamine and a metal hydride, preferably sodium borohydride, without the formation of the over-reduction by-products of the primary hydroxyl, as described in the scheme indicated below.

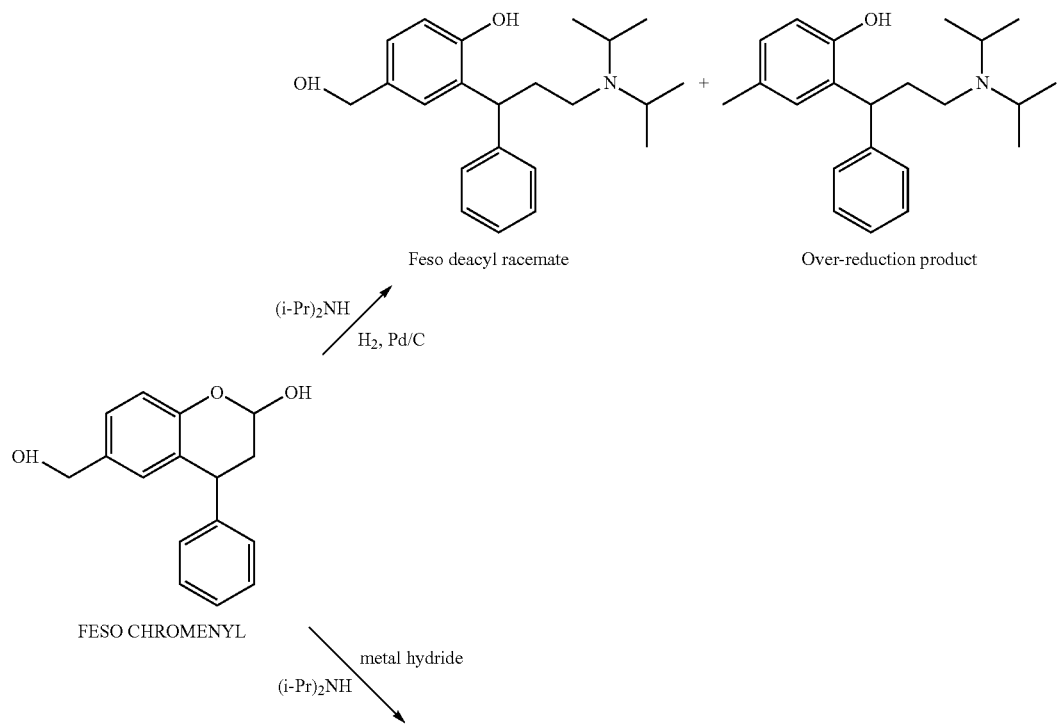

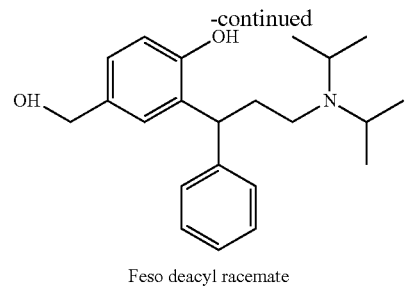

Feso deacyl racemate

In a preferred embodiment of the present invention, feso chromenyl is dissolved in an apolar organic solvent, such as for example toluene, dichloromethane or ethyl acetate; According to a particularly preferred aspect of the invention feso chromenyl is dissolved in toluene.

Diisopropylamine is added to the feso chromenyl solution. The diisopropylamine:feso chromenyl molar ratio is preferably comprised between 2 and 4 equivalents, even more preferably 3 equivalents of diisopropylamine with respect to feso chromenyl are reacted. The solution is brought to reflux, removing the water that is formed in the in reaction through azeotropic distillation.

The reaction mixture is cooled to a temperature preferably comprised between 0 and 10° C., even more preferably between 0 and 5° C., and a metal hydride is added, preferably in alcohol solution, such as for example sodium borohydride, lithium aluminium hydride or sodium cyanoborohydride, preferably sodium borohydride. Examples of alcohols to be used for dissolving the hydrides are $C_1$-$C_6$ aliphatic alcohols such as for example methanol, ethanol, isopropanol, isobutanol and the like. Methanol is particularly preferred. According to an aspect of the invention, the metal hydride:feso chromenyl molar ratio is comprised between 1 and 2 equivalents, preferably between 1 and 1.5 equivalents.

The transformation of feso deacyl raceme into (R)-feso deacyl can be conducted through any of the methods described by the literature, for example as disclosed by WO2007138440, herein incorporated for reference, using (R)-acetoxymandelic acid as the resolvent agent.

(R)-feso deacyl is an intermediate useful for the preparation of fesoterodine, in particular fesoterodine fumarate.

Thus, a further aspect of the present invention is the use of the (R)-feso deacyl obtained through the process of the present invention in the preparation of fesoterodine, in particular of the fesoterodine fumarate.

When applying the method described in WO2007138440, it was discovered that the (R)-feso deacyl crystallised by toluene, herein called form A, however contains, amounts of toluene exceeding 1300 ppm, which cannot be removed even after extensive drying.

Furthermore, it was unexpectedly discovered that by re-crystallising (R)-feso deacyl (preferably the aforementioned form A) from cyclohexane and acetone, there is obtained a product with a different crystalline form, called form B, which no longer contains measurable amounts of toluene and amounts below 800 ppm of acetone and cyclohexane, and which constitutes a further object of the present invention.

In a preferred embodiment of the present invention, (R)-feso deacyl is dissolved in a mixture of at least two solvents, one of which is at least an aprotic polar organic solvent, preferably an aliphatic ketone, more preferably acetone, methylethyl ketone, methyl isobutyl ketone, even more preferably acetone; and at least another solvent is an apolar organic solvent, preferably an aliphatic hydrocarbon, more preferably pentane, hexane, cyclohexane, heptane, even more preferably cyclohexane. In a preferred embodiment of the present invention a mixture of cyclohexane and acetone is used, preferably 10 to 30 volumes of cyclohexane per volume of acetone are used, even more preferably 25 volumes of cyclohexane per volume of acetone are used. According to an aspect of the invention, 1 to 20 volumes of said mixture of solvents per moles of (R)-feso deacyl are used, even more preferably from 3 to 8.

According to a further aspect of the invention, the mixture of the abovementioned solvents containing (R)-feso deacyl is brought to a temperature comprised between ambient temperature and reflux temperature of the mixture of the solvents. Preferably, the mixture is brought to a temperature comprised between 30° C. and 70° C., even more preferably between 45° C. and 65° C. The reaction mixture is thus cooled to a temperature comprised between 0° C. and ambient temperature, preferably at a temperature comprised between 15 and 25° C., even more preferably to about 20° C. The solid thus obtained is separated from the reaction mixture by means of filtration and dried, preferably under vacuum.

Figure 2:
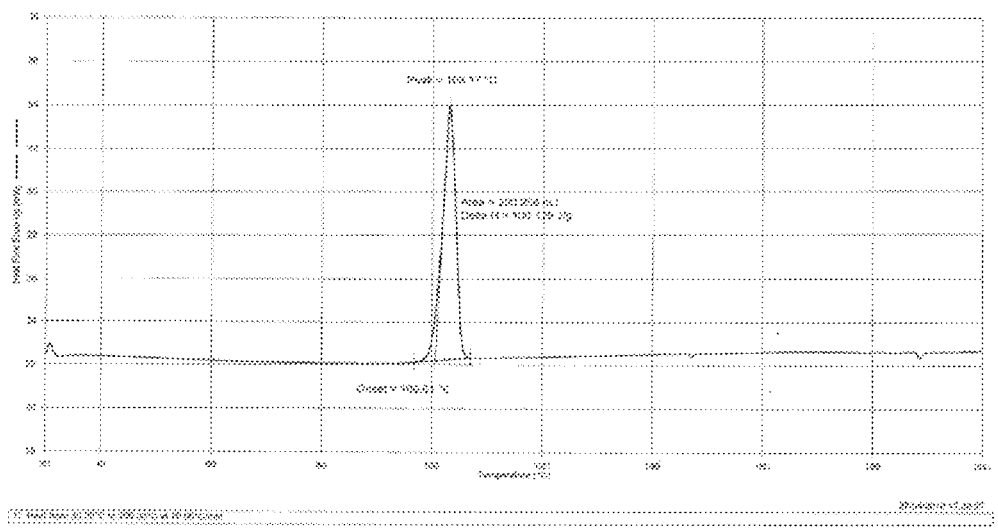
FIG. 2: DSC of the crystalline form A of the (R)-feso-deacyl
Figure 3:
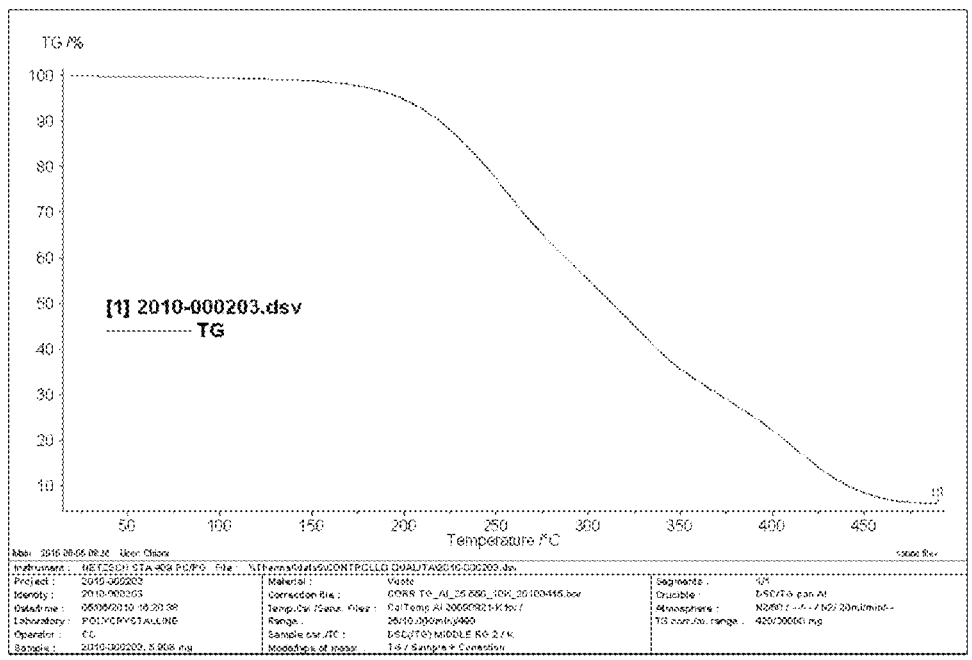
FIG. 3: TGA of the crystalline form A of the (R)-feso-deacyl
Figure 4:
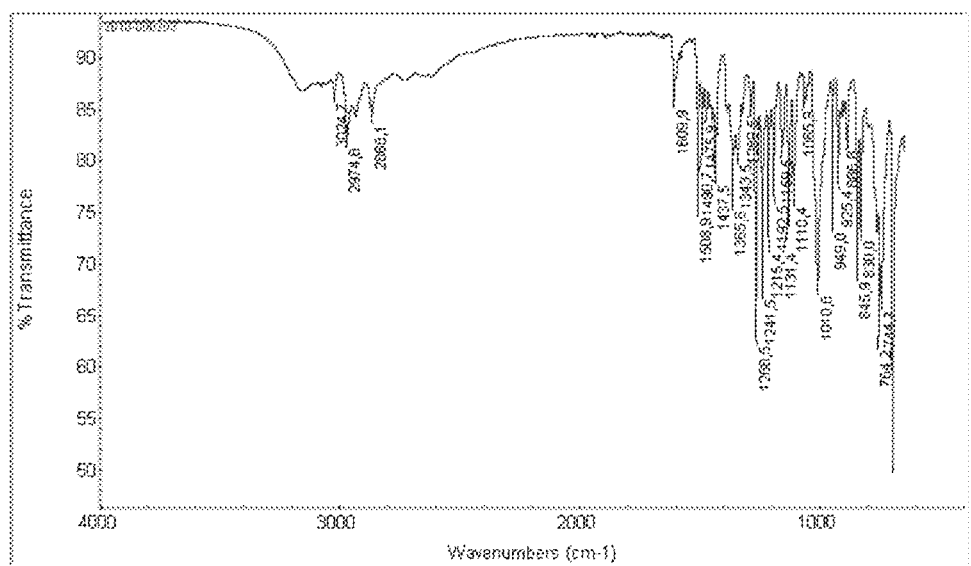
FIG. 4: FT-IR of the crystalline form A of the (R)-feso-deacyl

The (R)-feso-deacyl in crystalline form A is characterised by a powder X-ray diffractogram (PXRD) profile as indicated in FIG. 1, and/or by a DSC profile as indicated in FIG. 2, and/or by a TGA profile as indicated in FIG. 3 and/or by an FT-IR (ATR) profile as indicated in FIG. 4. The characteristic peaks which distinguish the aforementioned PXRD, DSC and FT-IR (ATR) charts are indicated below.

(R)-feso-deacyl in crystalline form A is characterised by the powder X-ray diffractogram (PXRD) profile indicated in FIG. 1, whose characteristic peaks are observed at the 2 theta positions: 8.59; 10.93; 11.45; 12.47; 13.23; 14.77; 15.33; 16.62; 17.20; 18.20; 18.53; 19.14; 20.05; 20.55; 21.79; 21.43; 23.25; 24.12; 25.33; 26.12; 26.95; 28.00; 28.73; and 29.65 degrees, with a ±0.1 degree margin of error on the value indicated for each peak (2 theta).

Further data characterising the PXRD diffractogram of such crystalline form is indicated in the following table.

TABLE 1

| Pos. [°2 Th.] | Height [cts] | FWHM [°2 Th.] | d-spacing [Å] | Rel. Int. [%] |
|---|---|---|---|---|
| 8.5869 | 6045.19 | 0.2342 | 10.29769 | 72.38 |
| 10.9321 | 261.26 | 0.2007 | 8.09332 | 3.13 |
| 11.4451 | 354.75 | 0.1004 | 7.73169 | 4.25 |
| 12.4745 | 4655.53 | 0.2509 | 7.09587 | 55.74 |
| 13.2344 | 3220.22 | 0.2509 | 6.69009 | 38.56 |
| 14.7338 | 6453.38 | 0.1338 | 6.01250 | 77.27 |
| 14.8273 | 6360.30 | 0.1004 | 5.97480 | 76.16 |
| 15.3260 | 8290.90 | 0.2509 | 5.78149 | 99.27 |
| 16.5523 | 5924.43 | 0.1171 | 5.35579 | 70.94 |
| 16.6813 | 6170.05 | 0.1338 | 5.31468 | 73.88 |
| 17.2015 | 134.28 | 0.1171 | 5.15511 | 1.61 |

TABLE 1-continued

| Pos. [°2 Th.] | Height [cts] | FWHM [°2 Th.] | d-spacing [Å] | Rel. Int. [%] |
|---|---|---|---|---|
| 18.1541 | 7289.87 | 0.1171 | 4.88670 | 87.29 |
| 18.2813 | 8351.53 | 0.1171 | 4.85298 | 100.00 |
| 18.5359 | 2017.70 | 0.0836 | 4.78688 | 24.16 |
| 19.1375 | 4053.13 | 0.2676 | 4.63776 | 48.53 |
| 19.9940 | 2447.12 | 0.1506 | 4.44097 | 29.30 |
| 20.1621 | 1774.12 | 0.0836 | 4.40431 | 21.24 |
| 20.5004 | 1014.77 | 0.1004 | 4.33240 | 12.15 |
| 20.6585 | 614.07 | 0.0669 | 4.29960 | 7.35 |
| 21.4206 | 550.98 | 0.1338 | 4.14832 | 6.60 |
| 21.7908 | 1244.54 | 0.1673 | 4.07868 | 14.90 |
| 22.4291 | 2598.30 | 0.2342 | 3.96403 | 31.11 |
| 23.1911 | 719.45 | 0.1224 | 3.83230 | 8.61 |
| 23.2993 | 764.34 | 0.1004 | 3.81790 | 9.15 |
| 24.1224 | 3047.98 | 0.1506 | 3.68947 | 36.50 |
| 25.2421 | 2126.87 | 0.0816 | 3.52537 | 25.47 |
| 25.3306 | 3142.49 | 0.1020 | 3.51325 | 37.63 |
| 25.4266 | 2783.62 | 0.0836 | 3.50311 | 33.33 |
| 26.1288 | 591.79 | 0.0836 | 3.41053 | 7.09 |
| 26.9001 | 1475.75 | 0.1632 | 3.31172 | 17.67 |
| 27.0352 | 1503.64 | 0.1171 | 3.29820 | 18.00 |
| 27.9943 | 419.90 | 0.0836 | 3.18736 | 5.03 |
| 28.7394 | 231.23 | 0.2007 | 3.10639 | 2.77 |
| 29.5877 | 855.66 | 0.0816 | 3.01674 | 10.25 |
| 29.6861 | 1063.76 | 0.0836 | 3.00945 | 12.74 |
| 30.5418 | 875.58 | 0.0836 | 2.92705 | 10.48 |
| 31.6160 | 253.40 | 0.2007 | 2.83001 | 3.03 |
| 32.0402 | 178.37 | 0.1338 | 2.79351 | 2.14 |
| 32.4908 | 89.24 | 0.1338 | 2.75578 | 1.07 |
| 33.0380 | 287.60 | 0.1004 | 2.71139 | 3.44 |
| 33.4000 | 159.77 | 0.1673 | 2.68282 | 1.91 |
| 33.9139 | 525.87 | 0.0836 | 2.64333 | 6.30 |
| 34.2482 | 259.16 | 0.1338 | 2.61830 | 3.10 |
| 34.6296 | 93.97 | 0.1673 | 2.59033 | 1.13 |
| 35.5328 | 202.39 | 0.1673 | 2.52653 | 2.42 |
| 36.2790 | 504.80 | 0.1632 | 2.47421 | 6.04 |
| 36.3793 | 618.05 | 0.0836 | 2.46966 | 7.40 |
| 36.6830 | 445.64 | 0.1673 | 2.44991 | 5.34 |
| 37.6632 | 98.61 | 0.2342 | 2.38837 | 1.18 |
| 38.0691 | 81.04 | 0.1004 | 2.36383 | 0.97 |
| 38.9408 | 173.01 | 0.2342 | 2.31290 | 2.07 |
| 39.4481 | 98.19 | 0.2007 | 2.28432 | 1.18 |

(R)-feso-deacyl in crystalline form A is characterised by the DSC profile indicated in FIG. 2. In such chart there is observed an exothermic peak with Peak onset at 100.61° C., Peak at 103.17° C. and enthalpy difference equivalent to 100.1 Joule/g (ΔH=−100.1 J/g).

(R)-feso-deacyl in crystalline form A is characterised by an FT-IR profile measured through the ATR (Attenuated Total Reflection) technique indicated in FIG. 4, whose characteristic peaks are observed at the wavelengths: 3024.7; 2974.8; 2868.1; 1609.9; 1508.9; 1490.7; 1475.9; 1437.5; 1365.8; 1343.5; 1288.5; 1268.5; 1241.5; 1215.4; 1192.5; 1158.5; 1131.4; 1110.4; 1065.9; 1010.8; 949.0; 925.4; 868.8; 845.9; 830.0; 764.2; 744.7 cm$^{-1}$, with a ±1 cm$^{-1}$ margin of error on the value indicated for each peak.

Figure 5:
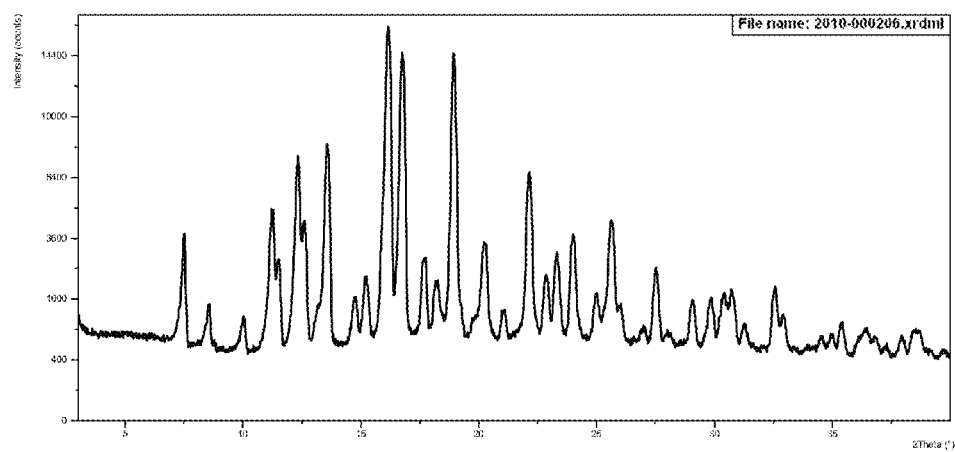
FIG. 5: PXRD of the crystalline form B of (R)-feso-deacyl
Figure 6:
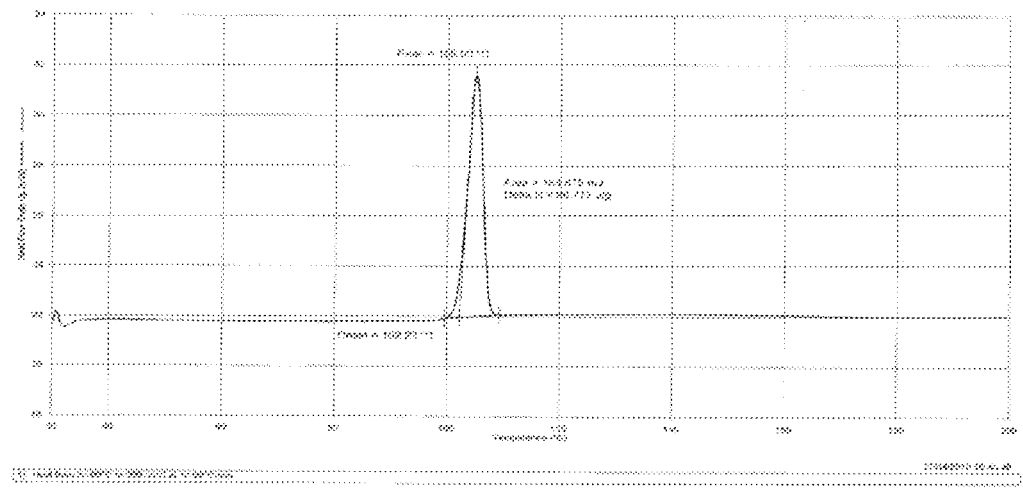
FIG. 6: DSC of the crystalline form B of (R)-feso-deacyl
Figure 7:
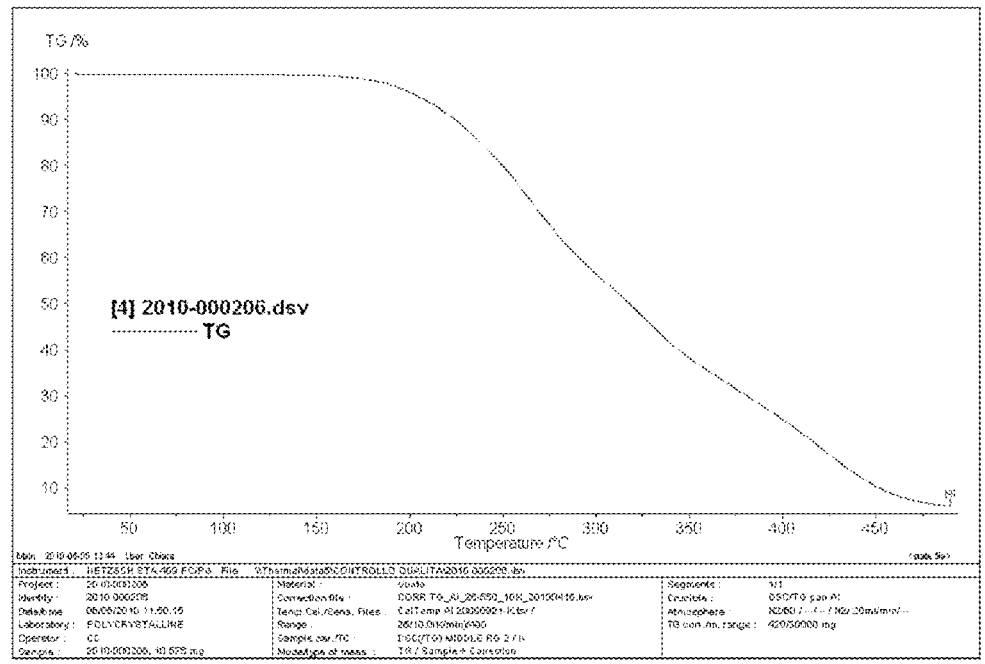
FIG. 7: TGA of the crystalline form B of (R)-feso-deacyl
Figure 8:
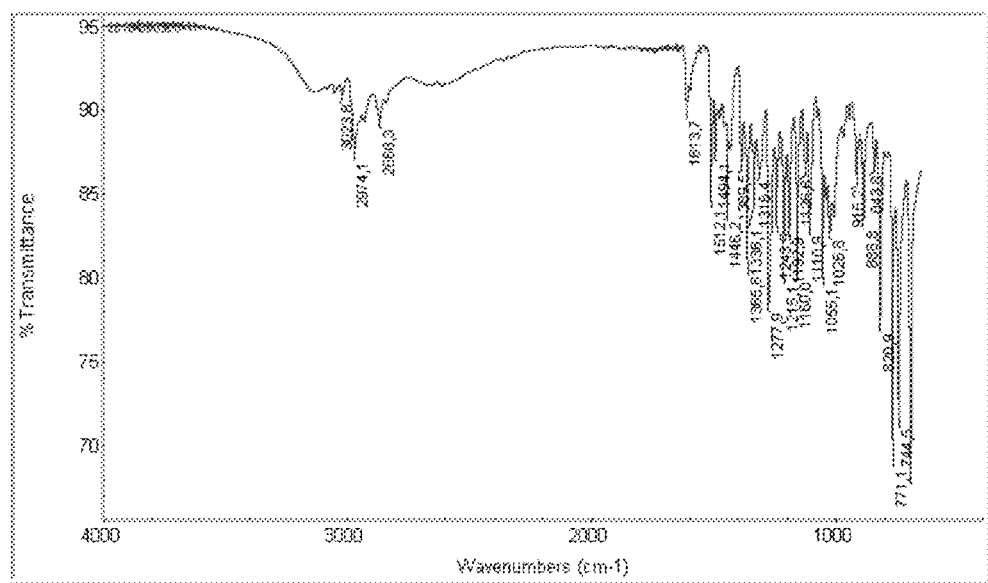
FIG. 8: FT-IR of the crystalline form B of (R)-feso-deacyl

(R)-feso-deacyl in crystalline form B is characterised by a powder X-ray diffractogram (PXRD) profile as indicated in FIG. 5, and/or by a DSC profile as indicated in FIG. 6, and/or by a TGA profile as indicated in FIG. 7 and/or by an FT-IR (ATR) profile as indicated in FIG. 8. The characteristic peaks that distinguish the aforementioned PXRD, DSC and FT-IR (ATR) charts are those indicated below.

(R)-feso-deacyl crystalline form B is characterised by the profile of the a powder X-ray diffractogram (PXRD) profile indicated in FIG. 5, whose characteristic peaks are observed at the 2 theta positions: 7.52; 8.58; 11.20; 11.54; 12.36; 12.69; 13.16; 13.65; 14.77; 15.22; 16.26; 16.86; 17.67; 18.20; 18.95; 20.31; 21.10; 22.15; 22.85; 23.25. 24.07; 25.03; 25.68; 27.50 and 29.00 degrees, with a ±0.1 degrees (2 theta) margin of error on the value indicated for each peak. The following table indicates further data characterising the PXRD diffractogram of such crystalline form.

TABLE 2

| Pos. [°2 Th.] | Height [cts] | FWHM [°2 Th.] | d-spacing [Å] | Rel. Int. [%] |
|---|---|---|---|---|
| 7.5256 | 2991.41 | 0.1171 | 11.74746 | 22.08 |
| 8.5837 | 829.05 | 0.1171 | 10.30154 | 6.12 |
| 10.0749 | 531.56 | 0.1004 | 8.77993 | 3.92 |
| 11.1504 | 3071.97 | 0.0669 | 7.93533 | 22.67 |
| 11.2799 | 4071.21 | 0.1171 | 7.84454 | 30.05 |
| 11.5483 | 1976.25 | 0.1506 | 7.66284 | 14.58 |
| 12.3615 | 6574.96 | 0.2007 | 7.16052 | 48.52 |
| 12.6904 | 2439.96 | 0.1840 | 6.97566 | 18.01 |
| 13.1606 | 663.86 | 0.1338 | 6.72747 | 4.90 |
| 13.6524 | 6019.30 | 0.2509 | 6.48619 | 44.42 |
| 14.7729 | 901.21 | 0.2007 | 5.99666 | 6.65 |
| 15.1744 | 1377.60 | 0.1171 | 5.83888 | 10.17 |
| 15.2797 | 1215.08 | 0.0836 | 5.79888 | 8.97 |
| 16.2559 | 11831.64 | 0.2509 | 5.45279 | 87.32 |
| 16.8596 | 9107.75 | 0.2676 | 5.25887 | 67.21 |
| 17.6204 | 1694.42 | 0.1171 | 5.03348 | 12.50 |
| 17.7678 | 1776.67 | 0.0836 | 4.99205 | 13.11 |
| 18.1041 | 839.38 | 0.1171 | 4.90008 | 6.19 |
| 18.2716 | 1163.65 | 0.0669 | 4.85552 | 8.59 |
| 18.9534 | 13550.20 | 0.2676 | 4.68237 | 100.00 |
| 19.7374 | 274.28 | 0.1338 | 4.49813 | 2.02 |
| 20.3171 | 2415.27 | 0.2342 | 4.37107 | 17.82 |
| 21.0946 | 541.30 | 0.0836 | 4.21169 | 3.99 |
| 22.0518 | 4611.57 | 0.0836 | 4.03099 | 34.03 |
| 22.2174 | 4585.00 | 0.1506 | 4.00131 | 33.84 |
| 22.8084 | 1316.90 | 0.1428 | 3.89572 | 9.72 |
| 22.9192 | 1186.23 | 0.1020 | 3.88678 | 8.75 |
| 23.2147 | 1557.70 | 0.0816 | 3.82846 | 11.50 |
| 23.3277 | 2132.34 | 0.1428 | 3.81017 | 15.74 |
| 24.0683 | 2551.37 | 0.2856 | 3.69457 | 18.83 |
| 25.0288 | 961.46 | 0.1020 | 3.55492 | 7.10 |
| 25.6830 | 3458.75 | 0.3264 | 3.46584 | 25.53 |
| 26.0396 | 670.92 | 0.1020 | 3.41917 | 4.95 |
| 27.0419 | 206.02 | 0.2856 | 3.29469 | 1.52 |
| 27.5024 | 1805.03 | 0.2856 | 3.24055 | 13.32 |
| 27.9749 | 147.23 | 0.2040 | 3.18688 | 1.09 |
| 28.9534 | 558.46 | 0.1020 | 3.08137 | 4.12 |
| 29.0715 | 890.73 | 0.1020 | 3.06912 | 6.57 |
| 29.7388 | 621.51 | 0.1020 | 3.00175 | 4.59 |
| 29.8784 | 886.79 | 0.1428 | 2.98804 | 6.54 |
| 30.4401 | 1006.03 | 0.0816 | 2.93417 | 7.42 |
| 30.7267 | 1178.88 | 0.1428 | 2.90746 | 8.70 |
| 31.2587 | 389.43 | 0.2448 | 2.85918 | 2.87 |
| 32.4825 | 1037.63 | 0.1020 | 2.75419 | 7.66 |
| 32.5712 | 1382.88 | 0.1428 | 2.74690 | 10.21 |
| 32.8853 | 656.97 | 0.1020 | 2.72137 | 4.85 |
| 34.5389 | 190.49 | 0.2448 | 2.59477 | 1.41 |
| 34.9916 | 232.80 | 0.2448 | 2.56223 | 1.72 |
| 35.4084 | 536.90 | 0.0612 | 2.53302 | 3.96 |
| 36.0645 | 185.47 | 0.2040 | 2.48843 | 1.37 |
| 36.4259 | 386.54 | 0.2448 | 2.46457 | 2.85 |
| 36.8330 | 223.25 | 0.2448 | 2.43826 | 1.65 |
| 37.3093 | 92.77 | 0.2448 | 2.40821 | 0.68 |
| 37.9709 | 239.53 | 0.1224 | 2.36776 | 1.77 |
| 38.4066 | 349.87 | 0.1836 | 2.34189 | 2.58 |
| 38.7327 | 333.94 | 0.2040 | 2.32293 | 2.46 |
| 39.6616 | 77.38 | 0.2040 | 2.27064 | 0.57 |

(R)-feso-deacyl in crystalline form B is characterized by the DSC profile indicated in FIG. 6. In such chart there is observed an exothermic peak with Peak onset at 102.23° C., Peak at 105.00° C. and enthalpy difference equivalent to 97.7 Joule/g (ΔH=−97.7 J/g).

(R)-feso-deacyl in crystalline form B is characterised by an FT-IR profile measured by means of the ATR (Attenuated Total Reflection) technique indicated in FIG. 8, whose characteristic peaks are observed at the wavelengths: 3023.8; 2974.1; 2868.3; 1613.7; 1512.1; 1494.1; 1446.2; 1389.5; 1365.6; 1336.1; 1316.4; 1277.9; 1243.9; 1215.1; 1192.9; 1160.0; 1136.6; 1110.9; 1055.1; 1026.8; 916.2; 888.8; 843.8;

820.9; 771.1; 744.5 cm$^{-1}$, with a ±1 cm$^{-1}$ margin of error on the value indicated for each peak.

The following examples are used to illustrate in detail the method subject of the present application and they do not constitute a restriction thereof in any manner whatsoever.

EXAMPLE 1

Preparation of 4-trimethylsilyloxymethyl-phenol 300 ml of dichloromethane followed by 60 g of triethylamine are added to 30 g of 4-hydroxymethyl-phenol introduced into a 500 ml flask maintained under a hydrogen atmosphere. The temperature of the obtained solution is brought to 10° C. and 64 g of trimethylsilyl chloride are added thereto in about one hour, keeping the temperature at 10° C. Thus, the temperature is left to spontaneously rise to 25° C., maintaining such conditions for one hour. Then, the reaction of the substrate is controlled under TLC. Upon ascertaining the disappearance of the initial product, 200 ml of an aqueous saturated NaCl solution are added and the two-phase system is stirred vigorously for 10' and then the two phases are decanted. The lower organic phase is washed with two 200 ml portions of deionised water and then concentrated to residue, obtaining a yellowish oil. Such residue is recovered using 500 ml of DMF in a 2-liter flask and a solution constituted by 3 g of Lithium acetate in 60 ml of water is added to the obtained solution. The mixture is maintained at 25° C. for one hour, then the removal of the trimethylsilyl group on the phenolic hydroxyl is controlled under TLC. Then, 650 ml of a saturated NaCl solution and 455 ml of toluene are added to the reaction mixture and the mixture is stirred vigorously for 10', then the two phases are left to decant. The upper organic phase is then washed with two 650 ml portions of deionised water and concentrated under vacuum, obtaining 33 g of the desired product (70% yield).

EXAMPLE 2

Preparation of 4-t-butyl-dimethylsilyloxymethyl-phenol 12 g of 4-hydroxymethyl-phenol, 180 ml of dichloromethane and 14 g of imidazole are introduced into a 250 ml flask. The mixture is cooled to 0° C. and a solution constituted by 32 g of t-butyl-dimethyl silyl chloride in 30 ml of dichloromethane are added thereto in about one hour. After adding it is left to recover at ambient temperature and such conditions are maintained for two hours. Thus the disappearance of the initial product is verified under TLC; if positive, 200 ml of a saturated NaCl solution are added, the mixture is stirred vigorously for 10', then the two phases are left to decant; the lower organic phase is washed using 200 ml of the saturated NaCl solution and 200 ml of deionised water, then concentrated under vacuum at 40° C. to obtain 34.1 g of a pale yellow oil. 340 ml of DMF and 34 ml of deionised water followed by 15.3 g of cesium carbonate are added to such residue. The mixture is stirred for two hours at 25° C., then it is diluted with 100 ml of deionised water and 170 ml of saturated NaCl solution and the mixture is extracted using 205 ml of toluene. The organic phase is washed using 100 ml of saturated NaCl solution and two 135 ml portions of deionised water, then evaporated to residue obtaining 22 g of an oil constituted by the desired product (94% yield)

EXAMPLE 3

Preparation of Feso Chromenyl from 4-trimethylsilyloxymethyl-phenol 8.5 g of 4-trimethylsilyloxymethyl-phenol are introduced into a 250 ml flask followed by 100 ml of toluene and 9.4 g of morpholine. The mixture is heated to 100° C. and 7.1 g of trans-cinnamaldehyde are added at such temperature. The mixture is maintained at 100° C. for 13 hours, then it is brought to 110° C. and it is maintained at such conditions for another 6 hours, during which the water formed in reaction is removed through the Dean-Stark device. At the end, the mixture is cooled to 60° C. and added with 60 ml of deionised water. It is stirred vigorously for 10', then the phases are left to separate. 30 ml of ethyl acetate and 50 ml of a 5% aqueous HCl solution are added to the organic phase. It is stirred at 50° C. for 30', then the organic phases are left to separate once again and the organic phase, brought to 25° C., is washed using two 50 ml portions of 2.5% aqueous solution of sodium bicarbonate and three 30 ml portions of deionised water. The organic phase is concentrated under vacuum at 40° C. up to residue. 25 ml of toluene and 15 ml of ethyl acetate are added to the residue, then heating up to the dissolution of oil. By cooling, there starts the precipitation of a yellowish solid, which after cooling the mixture at 0° C. and maintaining such conditions for 1 hour, is filtered and washed using 10 ml of 5:3 toluene ethyl acetate mixture at 0° C. and dried under vacuum at 50° C. for 4 hours. 6.6 g of feso chromenyl (60% yield) are thus obtained.

EXAMPLE 4

Preparation of Feso Chromenyl from 4-t-butyl-dimethylsilyloxymethyl-phenol 20 g of 4-t-butyl-dimethylsilyloxymethyl-phenol, 240 ml of toluene and 20.7 g of N-methyl-piperazine are introduced into a 500 ml flask. The mixture is heated to 100° C. and 13.6 g of trans-cinnamaldehyde are dripped thereonto. It is maintained at 100° C. for 16 hours, then the temperature is brought to 110° C. and it is maintained in such conditions for another 5 hours. The reaction mixture is cooled to 40° C. and 100 ml of deionised water are added thereto, it is stirred for 30' and the phases are left to separate. 60 ml of a 1 M solution of tetrabutylammonium fluoride under THF are added to the organic phase, the reaction mixture then being brought to 50° C. for two hours. Then it is cooled to 30° C. and 100 ml of deionised water are added, it is stirred for 30' and the phases are left to separate. 200 ml of a 5% aqueous HCl solution and 60 ml of acetate ethyl are added to the organic phase. The mixture is brought to 50° C. and such conditions are maintained for one hour. Once the mixture is cooled to 25° C., the phases are left to separate and the organic phase is washed in sequence using 200 ml of an aqueous solution of sodium bicarbonate at 10% and twice with 200 ml of deionised water. The organic phase is thus concentrated under vacuum at 40° C. up to residue, which is recovered with 20 ml of toluene and 10 ml of ethyl acetate, reconcentrating once again up to residue. The obtained residue is crystallised by 30 ml of toluene and 13 ml of ethyl acetate. This enables obtaining 14 g of a yellow solid constituted by the expected product (66% yield).

EXAMPLE 5

Preparation of Feso Deacyl Raceme 108 g of feso chromenyl 688 ml of toluene and 128.2 g of diisopropylamine are introduced into a 2000 ml flask. The mixture is heated up to reflux, observing the complete solubilisation of the undissolved products at 80° C. During reflux, the water that is formed in reaction is removed by azeotropic distillation through a Dean-Stark device. After ascertaining the disappearance of the initial product, the mixture is cooled to 25° C.

418 ml of methanol and 500 mg of sodium hydroxide pearls are introduced into another 3000 ml flask. After waiting for 30' for the complete dissolution of sodium hydroxide, the solution is cooled to 0° C. and 19.4 g of sodium borohydride are added, maintaining the temperature of the mixture between 0 and 5° C. The previously prepared toluene mixture is added to the obtained mixture at 0° C., being keen to avoid foaming. After adding it is maintained between 0 and 5° C. for 30', then 102 ml of a 5% sodium bicarbonate solution are added and it is stirred for 20'. Then, 554 ml of deionised water are added and the phases are left to separate after stirring. The organic phase is washed with 277 ml of deionised water and the resulting organic phase is evaporated under vacuum up to residue. 50 ml of acetonitrile are added to the residue and it is brought to residue once again. Then, 220 ml of acetonitrile are added to the residue, bringing the mixture to 60° C., with complete dissolution of the oil. By cooling to 25° C. there precipitates a white solid which is filtered, washed with two 20 ml portions of acetonitrile and dried under vacuum at 45° C. 114 g of the expected product are thus obtained. 79% yield.

EXAMPLE 6

Preparation of (R)-2-[3-(Diisopropylamino)-1-phenylpropyl]-4(hydroxymethyl)phenol (R)-2-acetoxy(phenyl)acetate 6000 ml of t-amyl alcohol and 412 g of feso deacyl raceme are introduced into a 10-liter reactor. The mixture is heated to 70° C. to completely dissolve the solid.

225 ml of t-amyl alcohol and 128 g of (R)-acetoxyphenylacetic acid are introduced into another 3000 ml reactor and the mixture is stirred at ambient temperature to completely dissolve the solid.

The (R)-2-acetoxyphenylacetic acid solution is added within two hours to the feso deacyl raceme solution maintained at 70° C. After introduction, it is maintained between 70 and 75° C. for 1 hour, then it is cooled to 65° C. in one hour, 200 mg of crystallisation seed constituted by (R)-2-[3-(Diisopropylamino)-1-phenylpropyl]-4(hydroxymethyl)phenol (R)-2-acetoxy(phenyl)acetate are added and it is maintained at 60° C. for two hours. Then it is cooled further to 25°. It is stirred for 12 hours at 25° C., then the obtained solid is filtered and it is washed with 1000 ml, 500 ml and 500 ml portions of t-amyl alcohol. The solid is dried under vacuum at 45° C. for 8 hours, obtaining 271 g of the expected product (42% yield).

EXAMPLE 7

Preparation of (R)-2-[3-(Diisopropylamino)-1-phenylpropyl]-4-(hydroxymethyl)phenol [(R)-feso deacyl]

260 g of (R)-2-[3-(Diisopropylamino)-1-phenylpropyl]-4-(hydroxymethyl)phenol (R)-2-acetoxy(phenyl)acetate and 2600 ml of toluene are introduced into a 10-liter reactor. 2600 ml of a 10% potassium carbonate solution are added to the mixture, brought to 50° C., and it is stirred for two hours. At the end, the two phases are left to separate and the organic phase is washed with 2000 ml of deionised water, still at the temperature of 50° C. The organic phase is then concentrated to residue, obtaining a white solid which is recovered with 400 ml of toluene and heated to 55° C. to obtain a complete solution. A white solid precipitates by cooling to 25° C. The suspension is maintained at 25° C. for two hours, then it is further cooled to 2° C. and maintained in such conditions for one hour. The obtained solid is filtered, washed with three 100 ml portions of toluene and dried under vacuum for 8 hours at 45° C., obtaining 116 g of the desired compound (70% yield).

PXRD, DSC, TGA and FT-IR of the obtained product are identical to those indicated for form A. The obtained product contains more than 1300 ppm of toluene. It can be recrystallised according to the method of the example 8, to obtain a toluene-free product.

EXAMPLE 8

Recrystallisation of (R)-2-[3-(Diisopropylamino)-1-phenylpropyl]-4-(hydroxymethyl)phenol from cyclohexane-acetone 30 g of (R)-2-[3-(Diisopropylamino)-1-phenylpropyl]-4-(hydroxymethyl)phenol obtained according to example 7 are introduced into a 250 ml flask alongside 154 ml of cyclohexane and 6.1 ml of acetone. The mixture is heated to 60° C., then it is slowly cooled to 20° C. The obtained solid is filtered and it is washed with a mixture of solvents constituted by 20 ml of cyclohexane and 1 ml of acetone, then it is dried under vacuum for 24 hours at 40° C. 27 g of the expected product (90% yield), which does not contain detectable amounts of toluene, are thus obtained. PXRD, DSC, TGA and FT-IR of the obtained product are identical to those indicated for form B. The characterisation of the crystalline forms A and B of (R)-2-[3-(Diisopropylamino)-1-phenylpropyl]-4-(hydroxymethyl)phenol was conducted through the following spectroscopic techniques, in the following experiment conditions:

PXRD (Powder X Ray Diffraction)
Experiment Conditions
Type of instrument: X'Pert PRO PANalytical
Type of measurement One scan
Measurement wavelength Cu Kα1
Material forming the anode: Cu
Voltage of the X-ray tube: 40
Current of the x-ray tube (mA): 40
Type of movement of the sample: Rotation
Time of rotation of the sample (s): 1.0
Thickness of the filter (mm): 0.020
Filter material: Ni
Name of the detector: X'Celerator
Type of detector: RTMS detector
Scanning axis: Gonio
Scanning range (°): 3.0000-39.9987
Amplitude of the measurement range (°): 0.0167
N.° of points: 2214
Scanning mode: Continuous
Counting time (s): 12.700
Application software: X'Pert Data Collector vs. 2.2d
Instrument control software: XPERT-PRO vs. 1.9B
Temperature Ambient temperature
FT-IR (ATR)
Experiment Conditions
Type of instrument: Nicolet FT-IR 6700 ThermoFischer
Spectral range (Standard): 7800-350 $cm^{-1}$
Spectral range (Option, CsI Optics): 6400-200 $cm^{-1}$
Spectral range (Option, Extended-Range Optics): 11000-375 $cm^{-1}$
Spectral range (Option, Multi-Range Optics): 27000-15 $cm^{-1}$ Optical resolution: 0.09 cm$^{-1}$
Peak to peak background noise (1 minute scan): <8.68×10−6 AU*
RMS background noise (1 minute scan): <1.95×10−6 AU*
Linearity in ordinate: 0.07% T
Wavelength precision: 0.01 cm−1
Minimum linear scanning speed: 0.158 cm/sec
Maximum linear scanning speed: 6.33 cm/sec
Number of scanning speed: 15
Quick scanning (Spectra/second @ 16 cm$^{-1}$, 32 cm$^{-1}$): 65, 95
Sample scanning number: 32
Number of background scans: 32
Resolution: 4,000 cm$^{-1}$
Gain of the sample: 8.0
Optical speed: 0.6329
Opening: 100.00
Detector: DTGS KBr
Beam splitter: KBr
Source: IR
DSC
Experiment Conditions
Instrument type: Perkin Elmer DSC-7
Calorimetric precision better than ±0.1%
Temperature precision ±0.1%
Temperature accuracy ±0.1%
Heating rate 10° C./min
Heating ramp 30° C. to 250° C.
Sample preparation 1 mg sample in a 50 µl capsule with holes
Thermal controller TAC 7/ΔX
TGA
Experiment Conditions
Type of instrument: STA 409 PC Luxx® Netzsch
Heating and cooling speed: 0.01 K/min; 50 K/min
TG resolution: up to 0.00002%
DSC resolution: <1 µW (K sensor)
DSC sensitivity 8 µV/mW (K sensor)
Atmosphere: Inert (Nitrogen)
Gas flow control: 2 flush gases and 1 protection gas
Flush gas: Nitrogen
Flush gas speed: 60 ml/min
Protection gas: Nitrogen
Protection gas speed: 20 ml/min
Crucible: DSC/TG pan Al
Heating speed: 10° C./min
DSC heating ramp: 30° C. a 280° C.
TGA heating ramp 40° C. a 500° C.

The invention claimed is:
1. Process for the preparation of 2-hydroxy-4-phenyl-3,4-dihydro-2H-chromen-6-yl-methanol of formula (I),

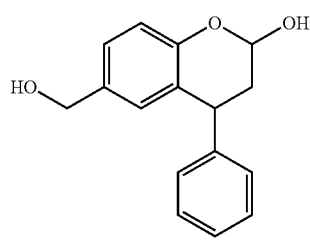

(I)

comprising:
a. silylating 4-hydroxymethylphenol of formula (A)

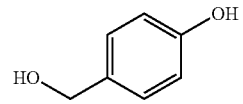

(A)

with a silylating agent to obtain a bis-silylated compound of formula (B)

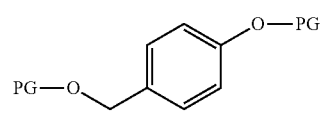

(B)

wherein PG is a silylated protective group;
b. selectively deprotecting the phenolic hydroxyl of the bis-silylated compound of formula (B) to obtain a mono-silylated compound of formula (C)

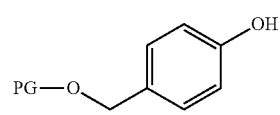

(C)

c. reacting the compound of formula (C) with trans-cinnamaldehyde and a cyclic secondary amine of formula (F)

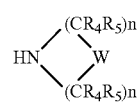

(F)

wherein
$R_4$ and $R_5$ are equal or different from each other and are hydrogen, $C_1$-$C_6$ alkyl or aryl and n varies between 1 and 4;
W is $(CH2)_m$ with m varying between 0 and 1, $NR_6$ (with $R_6=C_1$-$C_6$ alkyl or aryl), O or S;
to obtain a compound of formula (D)

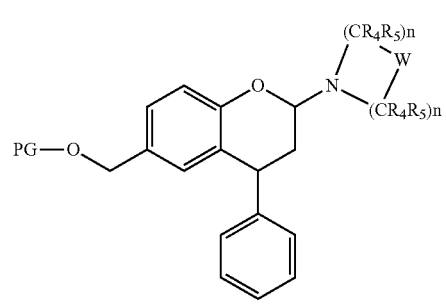

(D)

d. deprotecting the compound of formula (D), to obtain a compound of formula (E) and

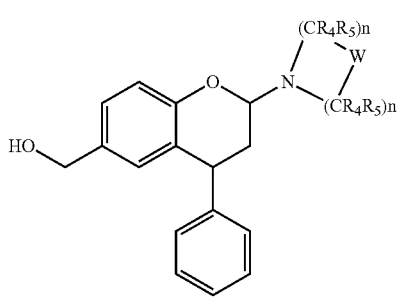

(E)

e. hydrolyzing the compound of formula (E) to provide the compound of formula (I).

2. The process according to claim 1, wherein said silylating agent is selected from among $R_1R_2R_3SiX$ where $R_1$, $R_2$, $R_3$ are $C_1$-$C_6$ linear or branched alkyl or aryl residues, X is a halogen or a sulfonate group;
$CY_3CO(Me_3Si)$=$NH(Me_3Si)$, where Y is hydrogen or halogen; or $(Me_3SiNH)_2C$=O.

3. The process according to claim 1, wherein said silylating agent is used in presence of a base.

4. The process according to claim 1, wherein said selective deprotection of the phenolic hydroxyl of the compound of formula (B) is conducted in the presence of a salt of an alkaline metal.

5. The process according to claim 1, wherein said cyclic secondary amine is selected from among morpholine, N-methyl-piperazine, N-benzyl-piperazine, pyrrolidine and piperazine.

6. The process according to claim 1, wherein said deprotection of the compound of formula (D) is conducted in presence of fluoride ion.

7. The process according to claim 1, wherein said hydrolysis occurs mixing the reaction mixture resulting from step (d) with an aqueous solution having a pH below 1.

8. The process according to claim 7, wherein 5 to 100 volumes of aqueous solution per volume of reaction mixture are used.

9. The process according to claim 1, wherein the compounds of formula (B), (D) and/or (E) are not isolated.

10. The process for preparation of (R)-2-[3-(diisopropylamino)-1-phenylpropyl]-4-(hydroxymethyl)phenol of formula (III),

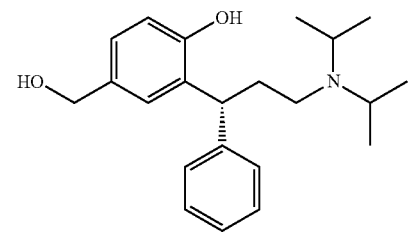

(III)

comprising:
a. obtaining 2-hydroxy-4-phenyl-3,4-dihydro-2H-chromen-6-yl-methanol of formula (I) according to the process of claim 1;
b. reductively aminating the 2-hydroxy-4-phenyl-3,4-dihydro-2H-chromen-6-yl-methanol of formula (I) in the presence of diisopropylamine and a metal hydride to obtain a 2-[3-(diisopropylamino)-1-phenylpropyl]-4-(hydroxymethyl)phenol racemate of formula (II),

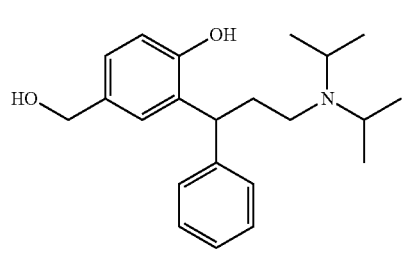

(II)

and
c. resolving the racemate of formula (II) to obtain (R)-2-[3-(diisopropylamino)-1-phenylpropyl]-4-(hydroxymethyl)phenol of formula (III) by crystallization with (R)-acetoxymandelic acid.

11. The process according to claim 10, wherein said metal hydride is sodium borohydride, lithium aluminum hydride, sodium cyanoborohydride.

12. The process for the preparation of fesoterodine or fesoterodine fumarate, comprising a process according to claim 1.

* * * * *